United States Patent [19]

Thimineur et al.

[11] Patent Number: 5,397,566
[45] Date of Patent: Mar. 14, 1995

[54] PERSONAL CARE COMPOSITIONS CONTAINING POLYALKYLSILOXANE COPOLYMERS

[75] Inventors: Raymond J. Thimineur, Scotia; Frank J. Traver, Troy; Virginia M. Van Valkenburgh, West Lebanon, all of N.Y.

[73] Assignee: General Electric Company, Waterford, N.Y.

[21] Appl. No.: 223,246

[22] Filed: Apr. 1, 1994

Related U.S. Application Data

[62] Division of Ser. No. 742,258, Aug. 8, 1991, Pat. No. 5,338,536.

[51] Int. Cl.$^6$ .......................... A61K 7/00; A61K 7/06
[52] U.S. Cl. .................... 424/70.12; 424/63; 424/64; 424/65; 424/401; 424/70.121; 514/844; 514/846; 514/847
[58] Field of Search .................... 424/70, 400, 401, 63, 424/64, 71, 65; 514/846, 847, 844

[56] References Cited

U.S. PATENT DOCUMENTS

| | | | |
|---|---|---|---|
| 3,418,353 | 12/1968 | Brown | 556/456 |
| 3,641,239 | 2/1972 | Mohriok | 424/64 |
| 4,574,082 | 3/1986 | Tietjen et al. | 424/63 |
| 4,652,386 | 3/1987 | Alberts et al. | 252/49.6 |
| 4,990,561 | 2/1991 | Yoshioka | 424/69 |
| 5,061,479 | 10/1991 | Grollier et al. | 424/64 |
| 5,106,611 | 4/1992 | Forestier et al. | 424/47 |
| 5,152,984 | 10/1992 | Varapath et al. | 424/70 |
| 5,160,730 | 11/1992 | Dubief et al. | 424/59 |
| 5,180,580 | 1/1993 | Halloran et al. | 424/71 |
| 5,180,584 | 1/1993 | Sebag et al. | 424/401 |
| 5,211,883 | 5/1993 | Yamashina et al. | 424/70 |
| 5,223,249 | 6/1993 | Forestier et al. | 424/70 |
| 5,240,698 | 8/1993 | Traver | 424/71 |
| 5,266,321 | 11/1993 | Shukuzaki et al. | 424/401 |
| 5,286,476 | 2/1994 | Nanba et al. | 424/47 |
| 5,288,482 | 2/1994 | Krzysik | 424/64 |
| 5,290,545 | 3/1994 | Halloran et al. | 424/70 |

FOREIGN PATENT DOCUMENTS

| | | |
|---|---|---|
| 0133964 | 3/1985 | European Pat. Off. . |
| 0177825 | 4/1986 | European Pat. Off. . |
| 0495596 | 7/1992 | European Pat. Off. . |
| 1041870 | 9/1966 | United Kingdom . |
| 1083476 | 9/1967 | United Kingdom . |
| 9109586 | 7/1991 | WIPO . |

*Primary Examiner*—Thurman K. Page
*Assistant Examiner*—Amy Hulina

[57] ABSTRACT

A personal care composition is provided, comprising (A) an effective amount of a polyalkylsiloxane copolymer having a melting point of from about $-40°$ to about $+40°$ C., and being selected from various specific polyalkylsiloxane copolymer fluids or polyalkylsiloxane copolymer resins; and (B) a cosmetically acceptable carrier medium, wherein the polyalkylsiloxane copolymer contains mixtures of linear lower alkyl side chains and linear higher alkyl side chains or mixtures of linear alkyl side chains and branched alkyl side chains. The polyalkylsiloxane copolymers used in the composition are fluids or soft waxes at body temperature and have improved application and payout and better substantivity and hair conditioning properties.

27 Claims, No Drawings

PERSONAL CARE COMPOSITIONS CONTAINING POLYALKYLSILOXANE COPOLYMERS

This is a divisional of application Ser. No. 07/742,258, filed on Aug. 8, 1991, now U.S. Pat. No. 5,338,536.

BACKGROUND OF THE INVENTION

The present invention is related to polyalkylsiloxane copolymers. More particularly, the present invention is directed to personal care compositions containing polyalkylsiloxane copolymer fluids or soft waxes as hair or skin treating agents.

Alkylpolysiloxanes are known in the art. Reference is made, for example, to U.S. Pat. Nos. 4,574,082 to Tietjen et al. and 3,418,353 (Brown).

In the patent to Tietjen et al., the internal silicon atoms are each bonded to a first alkyl group having 1–30 carbon atoms and a second alkyl group having 2 to 30 carbon atoms. The alkyl groups may be linear or branched. The alkylpolysiloxanes in Tietjen et al. are used in cosmetic products.

In the patent to Brown, the internal silicon atoms of the siloxane backbone are each bonded to a first organic group (designated as "R") which is methyl or phenyl and to a second organic group (designated as "$R^1$") which is a monovalent hydrocarbon radical having at least two carbon atoms and being free of aliphatic unsaturation, at least 50% of the hydrocarbon radicals in the second organic group being alkyl radicals containing at least 12 carbon atoms. In Brown, it is said to be particularly useful if the second organic group, $R^1$, is two different organic groups, i.e., $R^{11}$ and $R^{111}$, wherein $R^{11}$ is an alkyl radical containing at least 12 carbon atoms and $R^{111}$ is different from $R^{11}$ and represents a monovalent hydrocarbon radical free of aliphatic unsaturation and containing at least two carbon atoms. The alkylpolysiloxanes in Brown are used as release agents in molding applications.

Conventional alkylpolysiloxanes containing linear alkyl side chains of a specific length or linear alkyl side chains which are all either higher alkyl or lower alkyl become hard and brittle as the alkyl side chain becomes longer. Their hard and brittle nature makes these conventional alkylpolysiloxanes unsuitable for use in hair and skin care compositions, which require more fluid or gel-like polysiloxanes in order to have effective application and payout onto the hair or skin surface.

The present invention is based on the discovery that polyalkylsiloxane copolymers containing mixtures of linear lower alkyl side chains and linear higher alkyl side chains or mixtures of linear alkyl side chains and branched alkyl side chains will have a broader melting transition, as measured by a differential scanning calorimeter, and will display a lower onset point and a lower peak, which indicates melt point depression due to structural variations. Thus, the polyalkylsiloxane copolymers used in this invention will be fluids or soft waxes at body temperature and will have improved application and payout (i.e., spreadability) on hair and skin. Surprisingly, it has also been found that the polyalkylsiloxane copolymers used in this invention have better substantivity and hair conditioning properties than the conventional alkylpolysiloxanes described above.

SUMMARY OF THE INVENTION

In one aspect, the present invention provides a personal care composition, comprising:

(A) an effective amount of a polyalkylsiloxane copolymer having a melting point of from about $-40°$ C. to about $+40°$ C. and being selected from:

(1) a polyalkylsiloxane copolymer fluid comprising:
   (a) monofunctional units having the general formula $R_aR_b{}^1SiO_{\frac{1}{2}}$,
   (b) difunctional units having the general formula $RR^1SiO_{2/2}$, and
   (c) difunctional units having the general formula $RR^2SiO_{2/2}$, wherein the molar ratio of $R_aR_b{}^1SiO_{\frac{1}{2}}$ units to the sum of the $RR^1SiO_{2/2}$ units and $RR^2SiO_{2/2}$ units is from about 0.004:1 to about 0.5:1, and the molar ratio of $RR^1SiO_{2/2}$ units to $RR^2SiO_{2/2}$ units is from about 19:1 to about 3:7; or (2) a polyalkylsiloxane copolymer fluid comprising:
   (a) monofunctional units having the general formula $R_aR_b{}^1SiO_{\frac{1}{2}}$,
   (b) difunctional units having the general formula $RR^1SiO_{2/2}$, and
   (c) difunctional units having the general formula $RR^3SiO_{2/2}$, wherein the molar ratio of $R_aR_b{}^1SiO_{\frac{1}{2}}$ units to the sum of the $RR^1SiO_{2/2}$ units and $RR^3SiO_{2/2}$ units is from about 0.004:1 to about 0.5:1, and the molar ratio of $RR^1SiO_{2/2}$ units to $RR^3SiO_{2/2}$ units is from about 9:1 to about 1:19; or (3) a polyalkylsiloxane copolymer fluid comprising:
   (a) monofunctional units having the general formula $R_aR_b{}^1SiO_{\frac{1}{2}}$,
   (b) difunctional units having the general formula $RR^2SiO_{2/2}$, and
   (c) difunctional units having the general formula $RR^3SiO_{2/2}$, wherein the molar ratio of $R_aR_b{}^1SiO_{\frac{1}{2}}$ units to the sum of the $RR^2SiO_{2/2}$ units and $RR^3SiO_{2/2}$ units is from about 0.004:1 to about 0.5:1, and the molar ratio of $RR^2SiO_{2/2}$ units to $RR^3SiO_{2/2}$ units is from about 9:1 to about 1:19; or (4) a polyalkylsiloxane copolymer fluid comprising:
   (a) monofunctional units having the general formula $R_aR_b{}^1SiO_{\frac{1}{2}}$,
   (b) difunctional units having the general formula $RR^1SiO_{2/2}$,
   (c) difunctional units having the general formula $RR^2SiO_{2/2}$, and
   (d) difunctional units having the general formula $RR^3SiO_{2/2}$, wherein the molar ratio of $R_aR_b{}^1SiO_{\frac{1}{2}}$ units to the sum of the $RR^1SiO_{2/2}$ units, $RR^2SiO_{2/2}$ units, and $RR^3SiO_{2/2}$ units is from about 0.004:1 to about 0.5:1, the molar ratio of $RR^1SiO_{2/2}$ units to $RR^2SiO_{2/2}$ units is from about 19:1 to about 3:7; and the molar ratio of $RR^3SiO_{2/2}$ units to the sum of $RR^1SiO_{2/2}$ units and $RR^2SiO_{2/2}$ units is from about 1:9 to about 19:1;

(5) a polyalkylsiloxane copolymer resin comprising:

(a) monofunctional units having the general formula $R_cR_d{}^1SiO_{\frac{1}{2}}$,
(b) monofunctional units having the general formula $R_cR_d{}^2SiO_{\frac{1}{2}}$, and
(c) tetrafunctional units having the formula $SiO_{4/2}$,
wherein the molar ratio of the sum of $R_cR_d{}^1SiO_{\frac{1}{2}}$ units and $R_cR_d{}^2SiO_{\frac{1}{2}}$ units to $SiO_{4/2}$ units is from about 4:1 to about 3:2;

(6) a polyalkylsiloxane copolymer resin comprising:
(a) monofunctional units having the general formula $R_cR_d{}^1SiO_{\frac{1}{2}}$,
(b) monofunctional units having the general formula $R_cR_d{}^3SiO_{\frac{1}{2}}$, and
(c) tetrafunctional units having the formula $SiO_{4/2}$,
wherein the molar ratio of the sum of $R_cR_d{}^1SiO_{\frac{1}{2}}$ units and $R_cR_d{}^3SiO_{\frac{1}{2}}$ units to $SiO_{4/2}$ units is from about 4:1 to about 3:2, (7) a polyalkylsiloxane copolymer resin comprising:
(a) monofunctional units having the general formula $R_cR_d{}^2SiO_{\frac{1}{2}}$,
(b) monofunctional units having the general formula $R_cR_d{}^3SiO_{\frac{1}{2}}$, and
(c) tetrafunctional units having the formula $SiO_{4/2}$,
wherein the molar ratio of the sum of $R_cR_d{}^2SiO_{\frac{1}{2}}$ units and $R_cR_d{}^3SiO_{\frac{1}{2}}$ units to $SiO_{4/2}$ units is from about 4:1 to about 3:2;

(8) a polyalkylsiloxane copolymer resin comprising:
(a) monofunctional units having the general formula $R_cR_d{}^1SiO_{\frac{1}{2}}$,
(b) monofunctional units having the general formula $R_cR_d{}^2SiO_{\frac{1}{2}}$,
(c) monofunctional units having the general formula $R_cR_d{}^3SiO_{\frac{1}{2}}$, and
(d) tetrafunctional units having the formula $SiO_{4/2}$;
wherein the molar ratio of the sum of $R_cR_d{}^2SiO_{\frac{1}{2}}$ units, $R_cR_d{}^2SiO_{\frac{1}{2}}$ units and $R_cR_d{}^3SiO_{\frac{1}{2}}$ units to $SiO_{4/2}$ units is from about 4:1 to about 3:2;
wherein "a" is a number from 0 to 3, "b" is a number from 0 to 3, "a"+"b" is equal to 3, "c" is a number from 0 to 2, "d" is a number from 1 to 3, "c"+"d" is equal to 3, each R is independently an alkyl radical having from 1 to about 4 carbon atoms, a phenyl radical, or a phenethyl radical; each $R^1$ is independently a linear alkyl radical having from about 15 to about 36 carbon atoms; each $R^2$ is independently a linear alkyl radical having from about 6 to about 14 carbon atoms; and each $R^3$ is independently a branched alkyl radical having from about 5 to about 36 carbon atoms, the weighted average of $R^1$, $R^2$, and $R^3$ in the copolymer being sufficient to provide an average of from about 14 to about 30 carbon atoms in the sum of $R^1+R^2+R^3$; and
(B) a cosmetically acceptable carrier medium.

Other aspects of the present invention are directed to the copolymer (A) in the composition above, methods for treating hair and skin using the polyalkylsiloxane copolymer described above and methods for improving the conditioning ability of hair care compositions by adding the polyalkylsiloxane copolymer described above to such compositions.

DETAILED DESCRIPTION OF THE INVENTION

The present invention is directed to alkylpolysiloxane copolymers which contain at least two alkyl sidechains, one of which is a linear alkyl chain and the other is either a linear alkyl chain of a different length or a branched chain. The siloxane backbone chain may be either linear as in the case of copolymers (A)(1)–(A)(4) or it may be branched as in copolymers (A)(5)–(A)(8).

The alkylpolysiloxane copolymers of this invention are either a fluid or a soft wax at body temperature. Generally, the copolymers have a melting point of from about −40° to about +40° C., preferably from about −30° to about +35° C., and most preferably from about −20° to about +30° C. In skin care applications, it is preferred that the melting point be in the range of from about 20° C. to about 35° C. In hair care applications, it is preferred that the melting point be in the range of from about −30° C. to about +25° C.

In the formulas representing the units present in the copolymer, each R is independently an alkyl radical having from 1 to about 4 carbon atoms, a phenyl radical, or a phenethyl radical. Preferably, each R is methyl or ethyl and most preferably methyl. Each $R^1$ is independently a linear alkyl radical having from about 15 to about 36 carbon atoms; preferably from about 16 to about 24 carbon atoms, and most preferably from about 16 to about 22 carbon atoms. Each $R^2$ is independently a linear alkyl radical having from about 6 to about 14 carbon atoms, preferably from about 8 to about 14 carbon atoms, and most preferably from about 10 to about 14 carbon atoms. Each $R^3$ is independently a branched alkyl radical having from about 5 to about 36 carbon atoms, preferably from about 12 to about 30 carbon atoms, and most preferably from about 16 to about 28 carbon atoms.

In the copolymer used in the composition of this invention, the weighted average of $R^1$, $R^2$, and $R^3$ must be sufficient to provide an average of from about 14 to about 30, preferably from about 14 to about 26, and most preferably from about 14 to about 24 carbon atoms in the sum of $R^1+R^2+R^3$.

It is essential to the present invention that the weighted averages of $R^1$, $R^2$, and $R^3$ be sufficient to provide the average number of carbon atoms in the sum of $R^1+R^2+R^3$ recited hereinabove. If the average number of carbon atoms in the sum of $R^1+R^2+R^3$ is less than 14 in the case of either of the copolymers, the copolymer will be excessively thin and have reduced substantivity and lubricity (i.e., combability, spreadability, feel), and detackification properties. If the average number of carbon atoms in the sum of $R^1+R^2+R^3$ is more than 30, the copolymer will be a hard and brittle wax unsuitable for use in hair or skin care compositions.

In (A)(1) the molar ratio of $R_aR_b{}^1SiO_{\frac{1}{2}}$ units to the sum of the $RR^1SiO_{2/2}$ units and $RR^2SiO_{2/2}$ units is from about 0.004:1 to about 0.5:1, preferably from about 0.2:1 to about 0.01:1, and most preferably from about 0.1:1 to about 0.02:1. The molar ratio of $RR^1SiO_{2/2}$ units to $RR^2SiO_{2/2}$ units is from about 19:1 to about 3:7, preferably from about 9:1 to about 1:1, and most preferably from about 4:1 to about 1.5:1.

In (A)(2) the molar ratio of $R_aR_b{}^1SiO_{\frac{1}{2}}$ units to the sum of the $RR^1SiO_{2/2}$ units and $RR^3SiO_{2/2}$ units is from about 0.004:1 to about 0.5:1, preferably from about 0.2:1 to about 0.01:1, and most preferably from about 0.1:1 to about 0.02:1. The molar ratio of $RR^1SiO_{2/2}$ units to $RR^3SiO_{2/2}$ units is from about 9:1 to about 1:19, preferably from about 85:15 to about 15:85 and most preferably from about 4:1 to about 1:4.

In (A)(3) the molar ratio of $R_aR_b{}^1SiO_{\frac{1}{2}}$ units to the sum of the $RR^2SiO_{2/2}$ units and $RR^3SiO_{2/2}$ units is from about 0.004:1 to about 0.5:1, preferably from about 0.2:1 to about 0.01:1, and most preferably from about 0.1:1 to about 0.02:1. The molar ratio of $RR^2SiO_{2/2}$ units to $RR^3SiO_{2/2}$ units is from about 9:1 to about 1:19, preferably from about 15:85 to about 85:15, and most preferably from about 1:4 to about 4:1.

In (A)(4) the molar ratio of $R_aR_b{}^1SiO_{\frac{1}{2}}$ units to the sum of the $RR^2SiO_{2/2}$ units, $RR^2SiO_{2/2}$ units, and $RR^3SiO_{2/2}$ units is from about 0.004:1 to about 0.5:1, preferably from about 0.2:1 to about 0.01:1, and most preferably from about 0.1:1 to about 0.02:1. The molar ratio of $RR^1SiO_{2/2}$ units to $RR^2SiO_{2/2}$ units is from about 19:1 to about 3:7, preferably from about 9:1 to about 1:1, and most preferably from about 4:1 to about 1.5:1. The molar ratio of $RR^3SiO_{2/2}$ units to the sum of $RR^1SiO_{2/2}$ units and $RR^2SiO_{2/2}$ units is from about 1:9 to about 19:1, preferably from about 15:85 to about 85:15, and most preferably from about 1:4 to about 4:1.

In (A)(5) the molar ratio of the sum of $R_cR_d{}^1SiO_{\frac{1}{2}}$ units and $R_cR_d{}^2SiO_{\frac{1}{2}}$ units to $SiO_{4/2}$ units is from about 4:1 to about 3:2, preferably from about 77:23 to about 62:38, and most preferably from about 75:25 to about 65:35.

In (A)(6), the molar ratio of the sum of $R_cR_d{}^1SiO_{\frac{1}{2}}$ units and $R_cR_d{}^3SiO_{\frac{1}{2}}$ units to $SiO_{4/2}$ units is from about 4:1 to about 3:2, preferably from about 77:23 to about 62:38, and most preferably from about 75:25 to about 65:35.

In (A)(7) the molar ratio of the sum of $R_cR_d{}^2SiO_{\frac{1}{2}}$ units and $R_cR_d{}^3SiO_{\frac{1}{2}}$ units to $SiO_{4/2}$ units is from about 4:1 to about 3:2, preferably from about 77:23 to about 62:38, and most preferably from about 75:25 to about 65:35.

In (A)(8) the molar ratio of the sum of $R_cR_d{}^1SiO_{\frac{1}{2}}$ units, $R_cR_d{}^2SiO_{\frac{1}{2}}$ units and $R_cR_d{}^3SiO_{\frac{1}{2}}$ units to $SiO_{4/2}$ units is from about 4:1 to about 3:2, preferably from about 77:23 to about 62:38, and most preferably from about 75:25 to about 65:35.

In preferred embodiments of the formulas representing the units in copolymer (A), "a" is 3, "b" is 0, "c" is 2, and "d" is 1.

Copolymer (A) may further contain from about 0.5 to about 50 mol % of from about 0.5 to about 50 mol % of trifunctional units selected from (i) $RSiO_{3/2}$ units, (ii) $R^1SiO_{3/2}$ units, (iii) $R^2SiO_{3/2}$, (iv) $R^3SiO_{3/2}$, or (v) a mixture of two or more of the foregoing.

The alkylpolysiloxanes used in this invention can be made according to methods known in the art. For example, they can be made by reacting an organohydrogen polysiloxane and an olefinic hydrocarbon of the formula $CH_2=CHY$ wherein Y is a straight or branched chain monovalent hydrocarbon radical free of unsaturation in the presence of a conventional SiH-olefin addition catalyst. This method is described, for example, in U.S. Pat. Nos. 3,885,984 and 3,418,353, both of which are incorporated by reference herein.

The organohydrogenpolysiloxanes useful in the preparation of the alkylpolysiloxanes used in this invention can be linear fluids containing silicon-bonded hydrogen groups on the backbone of the chain or on one or more ends of the backbone chain. The linear organohydrogenpolysiloxanes are used to make the alkylpolysiloxane copolymers (A)(1)–(A)(4). The organohydrogenpolysiloxanes useful in the preparation of the alkylpolysiloxane copolymers (A)(5)–(A)(8) are resinous siloxanes containing hydrogen. These organohydrogenpolysiloxanes contain $R_2HSiO_{\frac{1}{2}}$ and $SiO_{4/2}$ units, and may also contain $R_3SiO_{\frac{1}{2}}$ units.

The alpha-olefin used to make the alkylpolysiloxanes can be linear (so as to form the $R^1$ and $R^2$ alkyl chains) or branched (so as to form the $R^3$ alkyl chain).

The reaction between the organohydrogenpolysiloxane and the alphaolefin is generally carried out in the presence of a conventional SiH-olefin addition catalyst. These catalysts are generally known in the art. Such catalysts include, for example, the elemental platinum catalysts, described in Bailey, U.S. Pat. No. 2,970,150, or the chloroplatinic acid catalyst described in Speier et al., U.S. Pat. No. 2,823,218. Other suitable catalysts include the platinum alcoholates described in Lamoreaux, U.S. Pat. No. 3,220,972, the platinum cyclopropane complexes described in Ashby, U.S. Pat. No. 3,159,662, and the platinum ethylene complex described in Ashby, U.S. Pat. No. 3,159,601. In addition to the platinum catalysts described hereinabove, other suitable addition reaction catalysts for use herein are other Group VIII metals, such as palladium, ruthenium, rhodium, and the like. All of the foregoing cited patents are hereby incorporated by reference herein.

Component (B) of the composition of this invention is a cosmetically acceptable carrier medium. The term "cosmetically acceptable" is intended to mean that it is suitable for contact with the human body and, more specifically, in contact with human hair. Aqueous carrier mediums are frequently used. Specific carrier mediums will vary according to the type of personal care product in which the composition of this invention will be used.

Examples of personal care products which may contain the compositions of this invention include lipsticks, eye-shadows, bronzes, blushes, lotions, handcreams, antiperspirants, shampoos, hair conditioners, an emollient, an antiseptic, a sunscreen agent, a cleansing agent, hair styling products, hair sprays, spritzes, and other skin care and hair care products.

In shampoos, the polyalkylsilicones used in this invention can be the sole hair conditioning agent present in the composition. It is possible that other conventional hair conditioning agents can be used, such as organic cationic hair conditioning agents. It is more common, however, to have a cationic hair conditioning agent present in a composition wherein the carder medium is a hair conditioner which can be used as a leave-on treatment or it can be rinsed off the hair. For example, the alkylsilicones used in this invention may be added to a cream rinse conditioner such as that used in U.S. Pat. No. 4,421,740 to Burton, which is hereby incorporated by reference herein. The Burton conditioner contains an aqueous emulsion of cetyl alcohol and a fatty alkyl quaternary ammonium compound as a cream rinse product. Examples of conditioning compounds used in the patent to Burton and which can be used in the present invention include stearyl dimethyl benzyl ammonium chloride and cetyl dimethyl amine oxide.

Another type of carrier medium which can be used in this invention is a composition dispensed from an aerosol container in the form of a collapsible foam aerosol hair product referred to as a "mousse" product. Such "mousse" products are described, for example, in U.S. Pat. No. 4,536,390 to Padden, which is hereby incorporated by reference herein.

Another type of carrier medium which can be used in this invention is a cosmetically acceptable solvent such as ethanol, isopropanol, volatile polydimethylsiloxane and polydimethylcyclosiloxane fluids.

If a self-pressurized aerosol spray is desired, then conventional propellants such as volatile hydrocarbons such as n-propane, isopropane, n-butane and isobutane can be used as well as compressed gases such as nitrogen and carbon dioxide.

Other carrier media will be apparent to those of ordinary skill in the art.

It is to be understood that the type and amount of polyalkylsilicone (A) used in the composition of this invention must be such that the composition remains stable.

Copolymer (A) is present in the personal care composition of this invention in an amount within the range of from about 0.25 to about 15 parts by weight per 100 parts of the carrier medium (B). The desired amount of the copolymer will generally vary according to the particular personal care application at hand. In hair care compositions, copolymer (A) is typically present within the range of from about 0.25 to about 5, preferably from about 0.5 to about 3, and most preferably from about 1 to about 2.5, parts by weight per 100 parts of the carrier medium (B). In skin care compositions, copolymer (A) is typically present within the range of from about 0.25 to about 15, preferably from about 1 to about 10, and most preferably from about 3 to about 7.5, parts by weight per 100 parts of the carrier medium (B).

Another embodiment of the present invention is a method for treating hair or skin using the composition of this invention. Skin may be treated by the alkyl silicone compositions of this invention by simply applying the alkyl silicone composition to the surface of the skin. In treating hair, the alkyl silicone or alkyl silicone composition is applied to the surface of the hair in any suitable manner such as by massaging the composition throughout the hair by hand, by dipping the hair into the composition, or by brushing or combing the alkyl silicone or alkyl silicone composition throughout the hair or by spraying.

In order to better able the artisan to practice the present invention, the following examples are provided by way of illustration and not by way of limitation. All parts and percentages are by weight unless otherwise noted.

EXPERIMENTAL

EXAMPLE 1

Example 1 illustrates the preparation of an alkylpolysiloxane copolymer within the scope of the present invention.

314 grams of a trimethylsilyl-chainstopped methyl hydrogenpolysiloxane having a viscosity of 15–25 centistokes at 25° C. and a hydrogen content of at about 1.6% by weight, 500 grams of toluene as solvent, and 200 grams of decamethylpentacyclosiloxane ($D^5$) as diluent were added to a three liter round bottom three neck flask equipped with a condensor, thermometer, heating mantle, agitator, thermal controller, addition funnel, and water trap. The pot was then heated to 120° C. to reflux the toluene and dry the vessel (free water removed in trap). Once the vessel was dried, about 50 grams of the hexadecene-1 were added to the reaction mixture, followed by one drop of Lamoreaux catalyst to initiate the addition reaction. 1200 grams of hexadecene-1 were added incrementally to the addition funnel. The balance of the olefin was added at a rate that would maintain the exotherm. During addition of the olefin, the pot was maintained at a temperature of between 115° C. and 130° C. and a total of 3 drops of Lamoreaux catalyst (i.e., chloroplatinic acid in octyl alcohol) was added to the reaction mixture. After addition of the olefin was complete, an infrared spectroscopy (I.R.) scan indicated that a small amount of SiH remained. An additional 80 grams of decene-1 were then added to the vessel. The addition reaction was complete when I.R. scanning showed total consumption of the SiH groups.

The reaction mixture was stripped to 200° C. at 5 mm pressure and sparged with nitrogen to remove the toluene and the $D^5$ diluent. The resulting stripped wax was then filtered into jars and allowed to solidify. Carbon Black, Fuller Earth, and Celite were used in a 1:2:4 ratio during filtration of the wax in order to assist in the preparation of colorless material. The resulting wax had a soft texture, was essentially colorless (melted) and nearly odorless (due to the removal of aromatic solvent during stripping and filtration) and had a melting point of about 34° C. When it was applied to the skin, the product spread easily and had a pleasant sensation and silky texture.

EXAMPLE 2

Example 2 illustrates the preparation of a hair conditioner using the alkylpolysiloxane copolymer prepared in Example 1.

A composition having the formulation shown in Table 1 below was prepared by blending the ingredients.

TABLE 1

| Example 2: Formulation | |
|---|---|
| Ingredient | Parts by Weight |
| Stearyl Alcohol | 1.80 |
| Cetyl Alcohol | 1.20 |
| Cetearth 20 | 1.00 |
| Varisoft ® DHT | 1.00 |
| Varisoft ® 250 | |
| Citric Acid | 0.05 |
| Stearamidopropyldiethylamine | 0.20 |
| Kathon CG | 1.00 |
| Copolymer Wax** | 1.00 |
| Water (distilled) | 92.75 |
| | 100* |

*pH adjusted to 4.5 with citric acid
**Copolymer Wax refers to a copolymer of hexadecylmethylsiloxane and decene-1

The composition prepared in Example 2 exhibited excellent conditioning properties such as wet and dry combing, softness, and shine.

EXAMPLE 3

Example 3 further illustrates the preparation of a hair conditioner using the alkylpolysiloxane copolymer prepared in Example 1.

A composition having the formulation shown in Table 2 below was prepared by blending the ingredients.

TABLE 2

| Example 3- Formulation | |
|---|---|
| Ingredient | Parts by Weight |
| Varisoft ® CRC | 5.00 |
| Cetearth 20 | 0.30 |
| Dowicil 200 | 0.10 |
| Copolymer Wax | 1.00 |
| Citric Acid | 0.05 |

TABLE 2-continued

| Example 3- Formulation | |
|---|---|
| Ingredient | Parts by Weight |
| Water (Distilled) | 93.55 |
| | 100* |

*pH adjusted to 4.5 with citric acid

The composition prepared in Example 3 exhibited excellent conditioning properties such as wet and dry combing, softness, and shine.

EXAMPLES 4–6

These examples illustrate the preparation of a physical blend of a branched alkylsiloxane and a linear alkylsiloxane.

These examples were carried out with the intention of softening or rendering gel-like an alkyl polysiloxane having a branched alkyl content of 6% by weight and an alkyl chain length of 16 carbon atoms.

Three physical blends were prepared.

The blend in Example 4 contained 50% by weight of an alkyl polysiloxane having a branched alkyl content of 6% by weight and an alkyl chain length of 16 carbon atoms and 50% by weight of an alkyl polysiloxane having a branched alkyl content of 57% by weight and an alkyl chain length of about 20–28 carbon atoms.

The blend in Example 5 contained 25% by weight of an alkyl polysiloxane having a branched alkyl content of 6% by weight and an alkyl chain length of 16 carbon atoms and 75% by weight of an alkyl polysiloxane having a branched alkyl content of 57% by weight and an alkyl chain length of about 20–28 carbon atoms.

The blend in Example 6 contained 75% by weight of an alkyl polysiloxane having a branched alkyl content of 6% by weight and an alkyl chain length of 16 carbon atoms and 25% by weight of an alkyl polysiloxane having a branched alkyl content of 57% by weight and an alkyl chain length of about 20–28 carbon atoms.

In each example, the two polymers were heated until liquid, mixed with a spatula, and then cooled to room temperature. Unexpectedly, the materials were incompatible. In each example, a white solid separated from a liquid material. The amount of solids corresponded to the amount of the alkylsiloxane containing the 16 carbon alkyl chain.

EXAMPLES 7–9

These examples illustrate the results obtained from a physically blend of two essentially linear alkylsiloxanes. The two polymers used were an alkyl polysiloxane wax having a branched alkyl content of 6% by weight and an alkyl chain length of 16 carbon atoms ("$C_{16}$ alkylsiloxane") and an alkyl polysiloxane wax having a branched alkyl content of 6% by weight and an alkyl chain length of 14 carbon atoms ("$C_{14}$ alkylsiloxane").

Three samples were prepared containing a blend of the two polymers described above.

The blend of Example 7 contained 50% by weight of $C_{14}$ alkylsiloxane and 50% by weight of $C_{16}$ alkylsiloxane. The blend of Example 8 contained 25% by weight of $C_{14}$ alkylsiloxane and 75% by weight of $C_{16}$ alkylsiloxane. The blend of Example 9 contained 75% by weight of $C_{14}$ alkylsiloxane and 25% by weight of $C_{16}$ alkylsiloxane.

In each example, the blend of polymers was weighed into an aluminum pan, heated until liquid, and then cooled to room temperature. The resulting blend was a soft solid. The DSC of the physical blend gave two distinct peaks, one starting at 0° C. with a peak at 20° C. and another peak starting at 34° C. with a peak at 38° C. These DSC results correspond to the individual peaks of the $C_{16}$ alkylsiloxane and the $C_{14}$ alkylsiloxane themselves.

EXAMPLE 10

A chemical blend of the "$C_{16}$ alkylsiloxane" and the "$C_{14}$ alkylsiloxane" used in Examples 7–9 was prepared according to the procedure described in Example 1. Unlike the physical blends prepared in Examples 7–9, which were soft solids, the chemical blend was a viscous liquid. The DSC results for the chemical blend also differed from the DSC results obtained for the physical blends of Examples 7–9. The DSC for the chemical blend gave one broad peak (with a shoulder) having an onset at 20° C., a peak at 25° C., and sparts at 33° C.

Thus, Examples 7–10 illustrate that the properties of physical blends are different from those of chemical blends.

Comparative Example A

A base conditioner was prepared by blending the following ingredients in the amounts indicated:

| | |
|---|---|
| Varisoft ® CRC | 4.00 parts by weight |
| Ceteareth-20 | 0.30 part by weight |
| Citric Acid | 0.05 part by weight |
| Kathon CG | 0.05 part by weight |
| Water | 95.60 by weight |

The pH of the blend was adjusted to 4.5 with additional citric acid. This blend was used as a control in the examples which follow.

Comparative Example B and Examples 11–14

Five compositions were prepared containing the base conditioner prepared in Comparative Example A and different alkylpolysiloxanes as shown in Table 3 below. In each composition, 1.25% by weight of the alkylpolysiloxane was incorporated into the base conditioner with a like reduction in water content to make up 100 parts of the formulation.

TABLE 3

| Examples 11–15: Alkylpolysiloxanes | |
|---|---|
| Example No. | Description of the Alkylpolysiloxane |
| B | $C_{14}$ liquid (5.6% branched) |
| 11 | $C_{16}$ soft wax (6.0% branched) |
| 12 | 50% $C_{14}$/50% $C_{16}$ thick liquid |
| 13 | 50% $C_{16}$–$C_{18}$ viscous liquid (32% branched) |
| 14 | 50% $C_{16-18}$/50% $C_{16}$ gel (19% branched) |

Each composition was tested on multiple hair swatches. Several properties were observed and rated against the control composition prepared in Comparative Example A, which contained no alkylsilicone. The ratings are as follows:

(−)(−) Much worse than the control
(−) Worse than the control
(0) Same as the control
(+) Better than the control
(+)(+) Much better than the control The properties measured of the five compositions and the corresponding ratings against the control are shown in Table 4 below.

TABLE 4

Comparative Example B and Examples 11–14: Properties

| Property | Ex. No. B | Ex. No. 11 | Ex. No. 12 | Ex. No. 13 | Ex. No. 14 |
|---|---|---|---|---|---|
| Wet Combing | (+) | (−) | (+) | (+)(+) | (−)(−) |
| Dry Combing | (+) | (−) | (0) | (+) | (−) |
| Shine | (+) | (0) | (+) | (0) | (0) |
| Softness | (+) | (+) | (+) | (0) | (0) |
| Static Control | (0) | (+) | (+) | (+) | (+) |
| Overall Appearance | (+)(+) | (0) | (+)(+) | (+) | (0) |

The compositions prepared in Comparative Example B and in Examples 12 and 13, which are liquids at room temperature, showed overall better results than the composition prepared in Comparative Example A.

The compositions prepared in Comparative Example B and in Examples 11–14 were then tested for their substantivity properties by application onto skin and removal by water. About ¼ cc of each composition was applied onto an approximately 5 centimeter area of shaved skin. The treated areas were immersed in warm water for 40 minutes with continual motion. Each area was allowed to air dry. A flow pen was used to mark each section. However, the compositions prepared in Examples 11 and 14 left obvious heavy films on the skin so it was not necessary the test further with this method. Each section was then wiped with a soft, absorbant chem-wipe to try to remove the mark. Silicone left on the skin will prevent the ink from contacting the skin and allow the mark to be readily wiped away.

Substantivity properties were measured using the following rating system:
1 ink stained skin—mark did not wipe off
2 less than control—but still significant ink staining
3 slight ink staining
4 no ink staining The ratings received by the compositions are shown in Table 5.

TABLE 5

Comparative Example A and Examples 11–14: Substantivity Properties

| Example No. | Rating |
|---|---|
| Comparative A | 1 |
| Comparative B | 3 |
| 11 | 4* |
| 12 | 3 |
| 13 | 3 |
| 14 | 4* |

*Did not test, but rating is based on the film left

The composition prepared in Example 14 was then formulated into an oil/water formulation (having an alkylpolysiloxane concentration of 7% by weight) and a water/oil formulation (having an alkylpolysiloxane concentration of 5% by weight) and tested for substantivity using the same method. Comparison examples were carried out using an oil/water and a water/oil formulation, neither of which contained the alkylpolysiloxane used in Example 14.

The oil/water and water/oil formulations containing the alkylpolysiloxanes each had better substantivity than their counterparts which did not contain the alkylpolysiloxane.

What is claimed is:
1. A personal care composition, comprising:
(A) from about 0.25 to about 15 parts by weight per 100 parts carrier medium of a polyalkylsiloxane copolymer having a melting point of from about −40° C. to about +40° C. and being selected from:
(1) a polyalkylsiloxane copolymer fluid comprising:
(a) monofunctional units having the general formula $R_aR_b{}^1SiO_{\frac{1}{2}}$,
(b) difunctional units having the general formula $RR^1SiO_{2/2}$, and
(c) difunctional units having the general formula $RR^2SiO_{2/2}$,
wherein the molar ratio of $R_aR_b{}^1SiO_{\frac{1}{2}}$ units to the sum of the $RR^1SiO_{2/2}$ units and $RR^2SiO_{2/2}$ units is from about 0.004:1 to about 0.5:1, and the molar ratio of $RR^1SiO_{2/2}$ units to $RR^2SiO_{2/2}$ units is from about 19:1 to about 3:7;
(2) a polyalkylsiloxane copolymer fluid comprising:
(a) monofunctional units having the general formula $R_aR_b{}^1SiO_{\frac{1}{2}}$,
(b) difunctional units having the general formula $RR^1SiO_{2/2}$, and
(c) difunctional units having the general formula $RR^3SiO_{2/2}$,
wherein the molar ratio of $R_aR_b{}^1SiO_{\frac{1}{2}}$ units to the sum of the $RR^1SiO_{2/2}$ units and $RR^3SiO_{2/2}$ units is from about 0.004:1 to about 0.5:1, and the molar ratio of $RR^1SiO_{2/2}$ units to $RR^3SiO_{2/2}$ units is from about 9:1 to about 1:19;
(3) a polyalkylsiloxane copolymer fluid comprising:
(a) monofunctional units having the general formula $R_aR_b{}^1SiO_{\frac{1}{2}}$,
(b) difunctional units having the general formula $RR^2SiO_{2/2}$, and
(c) difunctional units having the general formula $RR^3SiO_{2/2}$,
wherein the molar ratio of $R_aR_b{}^1SiO_{\frac{1}{2}}$ units to the sum of the $RR^2SiO_{2/2}$ units and $RR^3SiO_{2/2}$ units is from about 0.004:1 to about 0.5:1, and the molar ratio of $RR^2SiO_{2/2}$ units to $RR^3SiO_{2/2}$ units is from about 9:1 to about 1:19;
(4) a polyalkylsiloxane copolymer fluid comprising:
(a) monofunctional units having the general formula $R_aR_b{}^1SiO_{\frac{1}{2}}$,
(b) difunctional units having the general formula $RR^1SiO_{2/2}$,
(c) difunctional units having the general formula $RR^2SiO_{2/2}$, and
(d) difunctional units having the general formula $RR^3SiO_{2/2}$,
wherein the molar ratio of $R_aR_b{}^1SiO_{\frac{1}{2}}$ units to the sum of the $RR^1SiO_{2/2}$ units, $RR^2SiO_{2/2}$ units, and $RR^3SiO_{2/2}$ units is from about 0.004:1 to about 0.5:1, the molar ratio of $RR^1SiO_{2/2}$ units to $RR^2SiO_{2/2}$ units is from about 19:1 to about 30:70; and the molar ratio of $RR^3SiO_{2/2}$ units to the sum of $RR^1SiO_{2/2}$ units and $RR^2SiO_{2/2}$ units is from about 1:9 to about 19:1;
(5) a polyalkylsiloxane copolymer resin comprising:
(a) monofunctional units having the general formula $R_cR_d{}^1SiO_{\frac{1}{2}}$,

(b) monofunctional units having the general formula $R_cR_d{}^2SiO_{\frac{1}{2}}$, and
(c) tetrafunctional units having the formula $SiO_{4/2}$,
wherein the molar ratio of the sum of $R_cR_d{}^1SiO_{\frac{1}{2}}$ units and $R_cR_d{}^2SiO_{\frac{1}{2}}$ units to $SiO_{4/2}$ units is from about 4:1 to about 3:2;

(6) a polyalkylsiloxane copolymer resin comprising:
(a) monofunctional units having the general formula $R_cR_d{}^1SiO_{\frac{1}{2}}$,
(b) monofunctional units having the general formula $R_cR_d{}^3SiO_{\frac{1}{2}}$, and
(c) tetrafunctional units having the formula $SiO_{4/2}$,
wherein the molar ratio of the sum of $R_cR_d{}^1SiO_{\frac{1}{2}}$ units and $R_cR_d{}^3SiO_{\frac{1}{2}}$ units to $SiO_{4/2}$ units is from about 4:1 to about 3:2;

(7) a polyalkylsiloxane copolymer resin comprising:
(a) monofunctional units having the general formula $R_cR_d{}^2SiO_{\frac{1}{2}}$,
(b) monofunctional units having the general formula $R_cR_d{}^3SiO_{\frac{1}{2}}$, and
(c) tetrafunctional units having the formula $SiO_{4/2}$;
wherein the molar ratio of the sum of $R_cR_d{}^2SiO_{\frac{1}{2}}$ units and $R_cR_d{}^3SiO_{\frac{1}{2}}$ units to $SiO_{4/2}$ units is from about 4:1 to about 3:2; or (8) a polyalkylsiloxane copolymer resin comprising:
(a) monofunctional units having the general formula $R_cR_d{}^1SiO_{\frac{1}{2}}$,
(b) monofunctional units having the general formula $R_cR_d{}^2SiO_{\frac{1}{2}}$,
(c) monofunctional units having the general formula $R_cR_d{}^3SiO_{\frac{1}{2}}$, and
(d) tetrafunctional units having the formula $SiO_{4/2}$;
wherein the molar ratio of the sum of $R_cR_d{}^1SiO_{\frac{1}{2}}$ units, $R_cR_d{}^2SiO_{\frac{1}{2}}$ units and $R_cR_d{}^3SiO_{\frac{1}{2}}$ units to $SiO_{4/2}$ units is from about 4:1 to about 3:2; wherein "a" is a number from 0 to 3, "b" is a number from 0 to 3, "a"+"b" is equal to 3, "c" is a number from 0 to 2, "d" is a number from 1 to 3, "c"+"d" is equal to 3, each R is independently an alkyl radical having from 1 to about 4 carbon atoms, a phenyl radical, or a phenethyl radical; each $R^1$ is independently a linear alkyl radical having from about 15 to about 36 carbon atoms; each $R^2$ is independently a linear alkyl radical having from about 6 to about 14 carbon atoms; and each $R^3$ is independently a branched alkyl radical having from about 5 to about 36 carbon atoms, the weighted average of $R^1$, $R^2$, and $R^3$ in the copolymer being sufficient to provide an average of from about 14 to about 30 carbon atoms in the sum of $R^1+R^2+R^3$; and (B) a cosmetically acceptable carrier medium.

2. A composition according to claim 1 wherein each R is methyl, each $R^1$ is independently a linear alkyl radical having from about 16 to about 24 carbon atoms, each $R^2$ is independently a linear alkyl radical having from about 8 to about 14 carbon atoms, and each $R^3$ is independently a branched alkyl radical having from about 12 to about 30 carbon atoms.

3. A composition according to claim 2 wherein each $R^1$ is independently a linear alkyl radical having from about 16 to about 22 carbon atoms, each $R^2$ is independently a linear alkyl radical having from about 10 to about 14 carbon atoms, and each $R^3$ is independently a branched alkyl radical having from about 16 to about 28 carbon atoms.

4. A composition according to claim 1 wherein the weighted average of $R^1$, $R^2$, and $R^3$ is sufficient to provide an average of from about 14 to about 26 carbon atoms in the sum of $R^1+R^2+R^3$.

5. A composition according to claim 4 wherein the weighted average of $R^1$, $R^2$, and $R^3$ is sufficient to provide an average of from about 14 to about 24 carbon atoms in the sum of $R^1+R^2+R^3$.

6. A composition according to claim 1 wherein in (A)(1) the molar ratio of $R_aR_b{}^1SiO_{\frac{1}{2}}$ units to the sum of the $RR^1SiO_{2/2}$ units and $RR^2SiO_{2/2}$ units is from about 0.2:1 to about 0.01:1 and the molar ratio of $RR^1SiO_{2/2}$ units to $RR^2SiO_{2/2}$ units is from about 9:1 to about 1:1.

7. A composition according to claim 6 wherein in (A)(1) the molar ratio of $R_aR_b{}^1SiO_{\frac{1}{2}}$ units to the sum of the $RR^1SiO_{2/2}$ units and $RR^2SiO_{2/2}$ units is from about 0.1:1 to about 0.02:1 and the molar ratio of $RR^1SiO_{2/2}$ units to $RR^2SiO_{2/2}$ units is from about 4:1 to about 1.5:1.

8. A composition according to claim 1 wherein in (A)(2) the molar ratio of $R_aR_b{}^1SiO_{\frac{1}{2}}$ units to the sum of the $RR^1SiO_{2/2}$ units and $RR^3SiO_{2/2}$ units is from about 0.2:1 to about 0.01:1 and the molar ratio of $RR^1SiO_{2/2}$ units to $RR^3SiO_{2/2}$ units is from about 85:15 to about 15:85.

9. A composition according to claim 8 wherein in (A)(2) the molar ratio of $R_aR_b{}^1SiO_{\frac{1}{2}}$ units to the sum of the $RR^1SiO_{2/2}$ units and $RR^3SiO_{2/2}$ units is from about 0.1:1 to about 0.02:1 and the molar ratio of $RR^1SiO_{2/2}$ units to $RR^3SiO_{2/2}$ units is from about 4:1 to about 1:4.

10. A composition according to claim 1 wherein in (A)(3) the molar ratio of $R_aR_b{}^1SiO_{\frac{1}{2}}$ units to the sum of the $RR^2SiO_{2/2}$ units and $RR^3SiO_{2/2}$ units is from about 0.2:1 to about 0.01:1 and the molar ratio of $RR^2SiO_{2/2}$ units to $RR^3SiO_{2/2}$ units is from about 15:85 to about 85:15.

11. A composition according to claim 10 wherein in (A)(3) the molar ratio of $R_aR_b{}^1SiO_{\frac{1}{2}}$ units to the sum of the $RR^2SiO_{2/2}$ units and $RR^3SiO_{2/2}$ units is from about 0.1:1 to about 0.02:1 and the molar ratio of $RR^2SiO_{2/2}$ units to $RR^3SiO_{2/2}$ units is from about 4:1 to about 1:4.

12. A composition according to claim 1 wherein in (A)(4) the molar ratio of $R_aR_b{}^1SiO_{\frac{1}{2}}$ units to the sum of the $RR^2SiO_{2/2}$ units, $RR^2SiO_{2/2}$ units, and $RR^3SiO_{2/2}$ units is from about 0.2:1 to about 0.01:1, the molar ratio of $RR^1SiO_{2/2}$ units to $RR^2SiO_{2/2}$ units is from about 9:1 to about 1:1, and the molar ratio of $RR^3SiO_{2/2}$ units to the sum of $RR^1SiO_{2/2}$ units and $RR^2SiO_{2/2}$ units is from about 15:85 to about 85:15.

13. A composition according to claim 12 wherein in (A)(4) the molar ratio of $R_aR_b{}^1SiO_{\frac{1}{2}}$ units to the sum of the $RR^2SiO_{2/2}$ units, $RR^2SiO_{2/2}$ units, and $RR^3SiO_{2/2}$ units is from about 0.1:1 to about 0.02:1, the molar ratio of $RR^1SiO_{2/2}$ units to $RR^2SiO_{2/2}$ units is from about 4:1 to about 1.5:1, and the molar ratio of $RR^3SiO_{2/2}$ units to the sum of $RR^1SiO_{2/2}$ units and $RR^2SiO_{2/2}$ units is from about 1:4 to about 4:1.

14. A composition according to claim 1 wherein in (A)(5) the molar ratio of the sum of $R_cR_d{}^1SiO_{\frac{1}{2}}$ units and $R_cR_d{}^2SiO_{\frac{1}{2}}$ units to $SiO_{4/2}$ units is from about 77:23 to about 62:38.

15. A composition according to claim 14 wherein in (A)(5) the molar ratio of the sum of $R_cR_d{}^1SiO_{\frac{1}{2}}$ units and $R_cR_d{}^2SiO_{\frac{1}{2}}$ units to $SiO_{4/2}$ units is from about 75:25 to about 65:35.

16. A composition according to claim 1 wherein in (A)(6) the molar ratio of the sum of $R_cR_d{}^1SiO_{\frac{1}{2}}$ units and $R_cR_d{}^3SiO_{\frac{1}{2}}$ units to $SiO_{4/2}$ units is from about 77:23 to about 62:38.

17. A composition according to claim 16 wherein in (A)(6) the molar ratio of the sum of $R_cR_d{}^1SiO_{\frac{1}{2}}$ units and $R_cR_d{}^3SiO_{\frac{1}{2}}$ units to $SiO_{4/2}$ units is from about 75:25 to about 65:35.

18. A composition according to claim 1 wherein in (A)(7) the molar ratio of the sum of $R_cR_d{}^2SiO_{\frac{1}{2}}$ units and $R_cR_d{}^3SiO_{\frac{1}{2}}$ units to $SiO_{4/2}$ units is from about 77:23 to about 62:38.

19. A composition according to claim 18 wherein in (A)(7) the molar ratio of the sum of $R_cR_d{}^2SiO_{\frac{1}{2}}$ units and $R_cR_d{}^3SiO_{\frac{1}{2}}$ units to $SiO_{4/2}$ units is from about 75:25 to about 65:35.

20. A composition according to claim 1 wherein in (A)(8) the molar ratio of the sum of $R_cR_d{}^1SiO_{\frac{1}{2}}$ units, $R_cR_d{}^2SiO_{\frac{1}{2}}$ units and $R_cR_d{}^3SiO_{\frac{1}{2}}$ units to $SiO_{4/2}$ units is from about 77:23 to about 62:38.

21. A composition according to claim 20 wherein in (A)(8) the molar ratio of the sum of $R_cR_d{}^1SiO_{\frac{1}{2}}$ units, $R_cR_d{}^2SiO_{\frac{1}{2}}$ units and $R_cR_d{}^3SiO_{\frac{1}{2}}$ units to $SiO_{4/2}$ units is from about 75:25 to about 65:35.

22. A composition according to claim 1 wherein "a" is 3, "b" is 0, "c" is 2, and "d" is 1.

23. A composition according to claim 1 wherein copolymer (A) further comprises from about 0.5 to about 50 mol % of trifunctional units selected from (i) $RSiO_{3/2}$ units, (ii) $R^1SiO_{3/2}$ units, (iii) $R^2SiO_{3/2}$, (iv) $R^3SiO_{3/2}$, or (v) a mixture of two or more of the foregoing.

24. A composition according to claim 1 wherein the copolymer has a melting point of from about $-30°$ C. to about $+35°$ C.

25. A composition according to claim 24 wherein the copolymer has a melting point of from about $-20°$ C. to about $+30°$ C.

26. A composition according to claim 1 wherein the copolymer has a melting point of from about 20° C. to about 35° C.

27. A composition according to claim 1 wherein the copolymer has a melting point of from about $-30°$ C. to about $+25°$ C.

* * * * *